United States Patent [19]

Wandell

[11] Plant 4,979

[45] Feb. 1, 1983

[54] SUGAR MAPLE TREE NAMED LEGACY

[76] Inventor: Willet N. Wandell, Myra Station Rd., Rte. 3, Box 158, Urbana, Ill. 61801

[21] Appl. No.: 245,153

[22] Filed: Mar. 18, 1981

[51] Int. Cl.[3] ..... A01H 5/00
[52] U.S. Cl. ..... Plt./51
[58] Field of Search ..... Plt./51

[56] References Cited

U.S. PATENT DOCUMENTS

P.P. 2,339 1/1964 Flemer ..... Plt./51

*Primary Examiner*—James R. Feyrer
*Attorney, Agent, or Firm*—Wm. A. Snow

[57] ABSTRACT

This disclosure concerns a new and distinct variety of *Acer saccharum* (commonly known as sugar maple tree) characterized by its exceptional growth habit with thick, leathery leaves, a tight compact crown with a heavy distribution of leaves which are not subject to tatter, and its extreme ease of propagation.

4 Drawing Figures

BACKGROUND OF THE INVENTION

This new variety of sugar maple tree was found growing in a planting of sugar maple seedling beds at my Duncan Nursery in Champaign, Ill., in the Spring of 1967, and grew to a height of six feet in the first year. Each year since it has had a robust growth habit. As the tree grew, it exhibited thicker, leathery, darker color leaves with a definite sheen or luster than other maple tree leaves in the stand. More leaves appear at the crown than other trees in adjacent rows of sugar maple trees. I now have 200 trees in my nursery at Urbana, Ill., all propagated by budding.

SUMMARY OF THE INVENTION

A new and distinct cultivar of sugar maple tree characterized by its exceptional growth habit with thick, leathery leaves with a definite sheen or luster, a tight compact crown with a heavy distribution of leaves not subject to tatter as are sugar maples grown in a wide midwest area of the United States, and extreme ease of propagation with new bud growth exhibiting tall, straight stems and many well-distributed branches, the leaves having a protective wax by cutin layer which is 1.5 times thicker than normal maple tree leaves in the stand.

BRIEF DESCRIPTION OF THE DRAWINGS

The upper photograph shows my new variety of sugar maple tree as it appeared in 1980 after nine growing seasons following transplant in a nursery field.

The lower photograph shows the tree during late Fall.

The pen-and-ink drawing discloses the mature leaves, stems and a bud. The second photograph shows the mature leaves and stems. The second photograph discloses the upper and lower sides of the leaf.

DETAILED DESCRIPTION OF THE NEW PLANT VARIETY

The following is a detailed description of my new variety of sugar maple tree, the stated observations having been made of trees growing in my nurseries at Champaign and Urbana, Ill., both cities in Champaign County.

Origin: Seedling.
Parentage and classification: Variety of *Acer saccharum.*
Form: Tree.
Shape: Upright and pyramidal.
Height: From 25 to 30 feet, growing 5 feet during second year after budding, including branching. Tree grows with straight trunk and is very robust.
Trunk size: 11.43 cm. one foot above ground.
Growth rate: Relatively faster than other maple trees in the stand by about 38.2 percent for the species.
Bark: Dark gray, somewhat smooth with a tendency to be definitely scaled.
Branches:
*Angle of attachment.*—62°.
*Size.*—4 cm.
*Spacing.*—18.4 cm.
Leaves: Mature.
*Length.*—9 to 14 cm.
*Width.*—12 to 19 cm.
*Form.*—Deciduous, opposite, 2-ranked, firm in texture, palmately lobed with 3 large lobes and 3 smaller basal lobes, the bases being subcordate, the lobes long acuminate and coarsely toothed. Leaves 1.6 times thicker and having a protective wax by cutin layer which is 1.5 times thicker than normal maple tree leaves in the Midwest area.
*Veins.*—Palmately arranged, reticulate.
*Petioles.*—6–13 cm. in length.
*Texture.*—Firm and leathery.
*Pubescence distribution.*—Confined to tufts of hairs in the axels of veins on the lower leaf surface.

Comparison Table

| | Legacy | Green Mt. PP 2339 | Bonfire PP 3817 | Goldspire PP2917 | Sentry |
|---|---|---|---|---|---|
| Leaf thickness (in microns) | 268 | 222 | 182 | 245 | 208 |
| Cuticle | 4.0 | 2.5 | 2.0 | 2.0 | 2.1 |
| Mesophyll | 129 | 166 | 78 | 114 | 90 |
| Parenchyma | 118 | 106 | 90 | 108 | 99 |
| Epidermal | | | | | |

-continued

| | Comparison Table | | | | |
|---|---|---|---|---|---|
| | Legacy | Green Mt. PP 2339 | Bonfire PP 3817 | Goldspire PP2917 | Sentry |
| layer | 28 | 15 | 13 | 25 | 16 |

Winter buds: Sessile, pubescent, tapering, with 10–14 4-ranked bud scales, the terminal buds 6 to 7 mm. long, the lateral buds opposite, 4-ranked, 3 to 6 mm. long, with a good survival rate during the winter months.

Flowers and fruit: Unknown since *Acer saccharum* sugar maple trees do not bear until they are 30 years old.

Fall color: Various shades of reds, pinks and orange.

This variety resembles a sugar maple tree (*Acer saccharum*) and clearly distinguishes from other sugar maple trees by its rapid growth habit in the stand growing under similar field conditions, by about 38.2 percentum, its darker colored and abundance of thicker leaves with good sheen or luster having a protective wax by cutin layer 1.5 times thicker than normal sugar maple trees in the stand, its heavier corwn permitting many more leaves than usual in sugar maple trees grown in the Midwest area, holding its distinguishing characteristics through propagation by budding, and freedom from leaf tatter during all seasons as exhibited by sugar maple trees in a wide area of the Midwest, the buds having a good survival rate through the winter months in the Midwest and outstanding growth through succeeding years.

I claim:

1. A new and distinct variety of sugar maple tree, substantially as herein shown and described, characterized by its relatively dense and fast growth of 38.2 percentum better than other sugar maple trees in the same stand, freedom from leaf tatter during all seasons as exhibited by sugar maple trees in a wide area of the Midwest, numerous strategically placed branches, an abundance of dark colored, leathery leaves with more leaves on the tight, compact crown, its relative ease of propagation and an excellent survival rate of buds through the winter months, with leaves having a protective wax by cutin layer which is 1.5 times thicker than leaves on ordinary sugar maple trees in the stand, the leaves having a protective wax by cutin which is 1.5 times thicker than normal sugar maple trees.

* * * * *

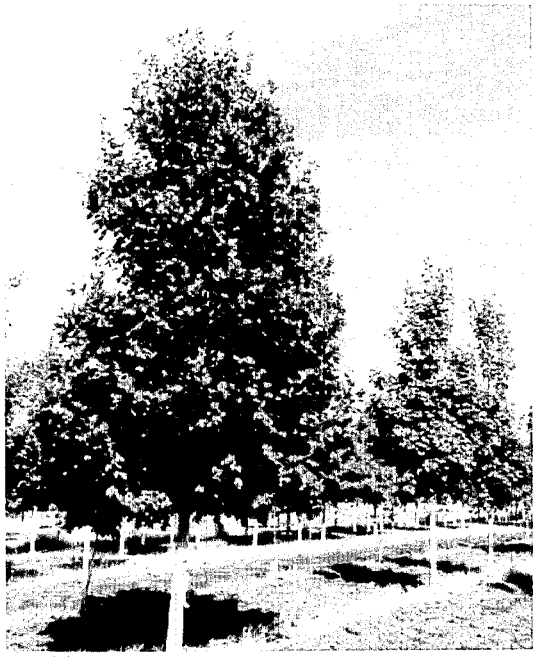
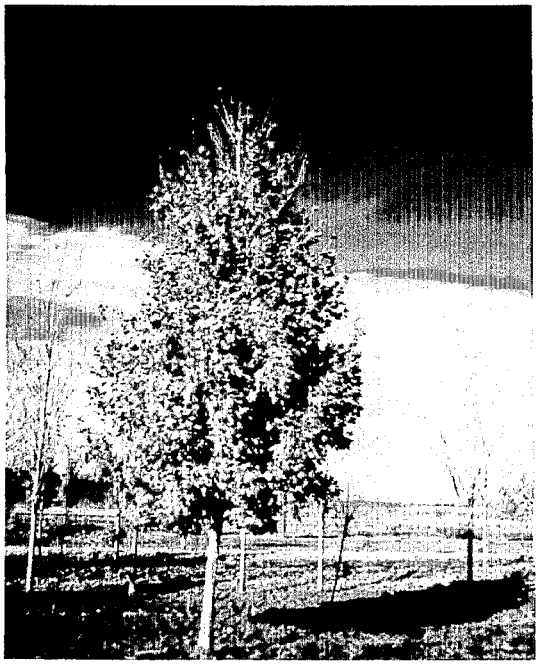

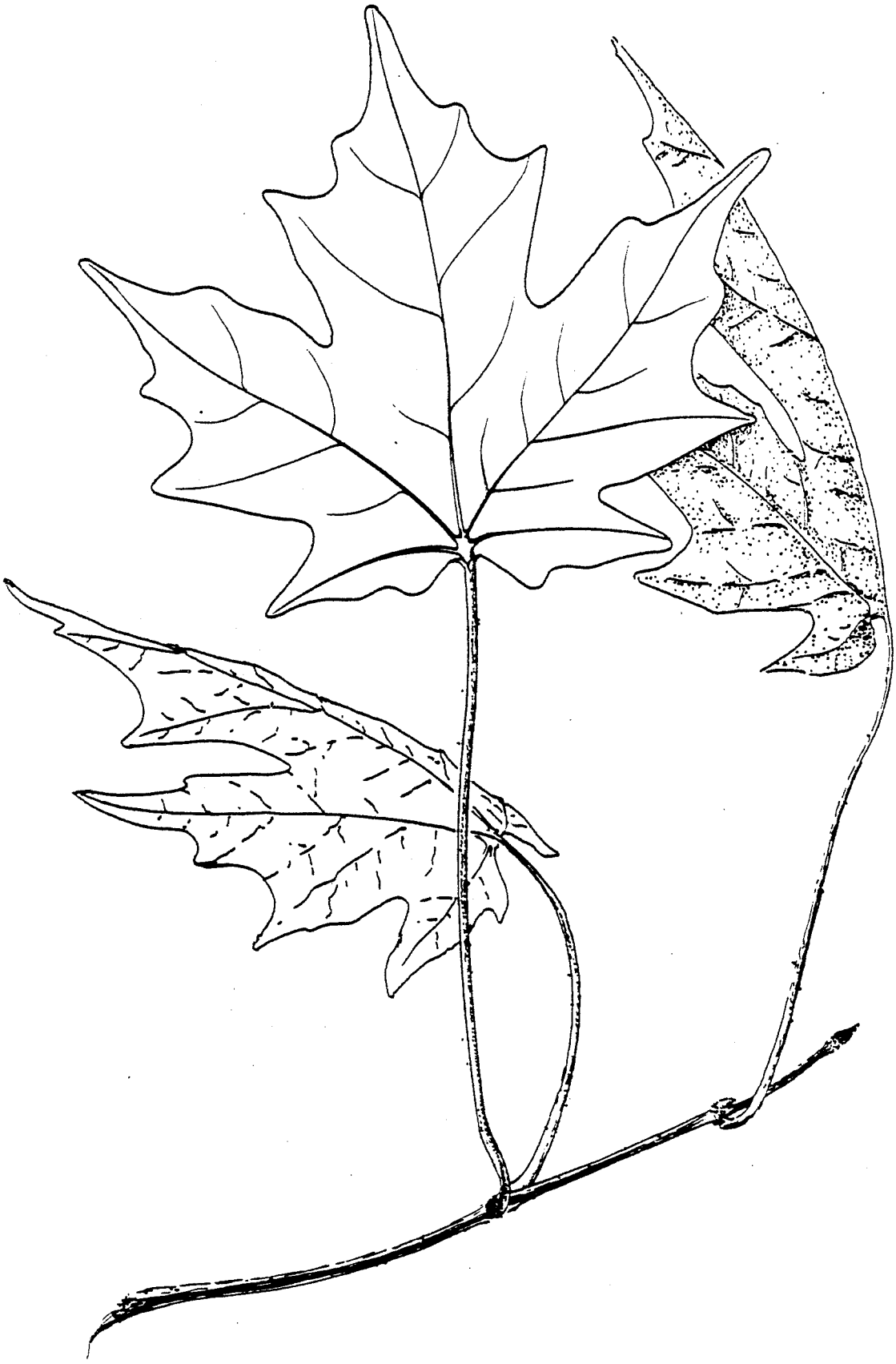

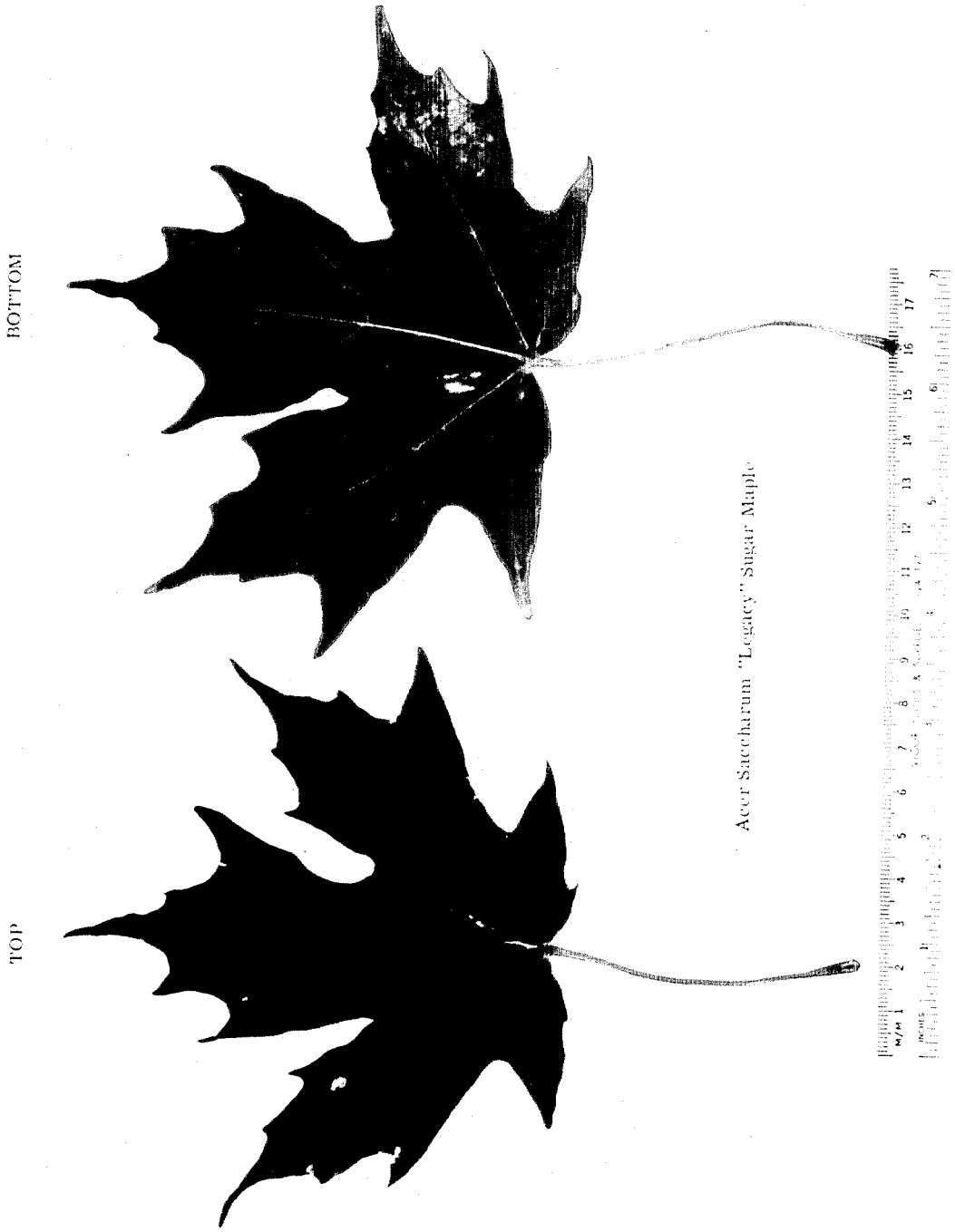
BOTTOM
TOP
Acer Saccharum "Legacy" Sugar Maple